United States Patent
Guo et al.

(10) Patent No.: US 9,675,368 B2
(45) Date of Patent: Jun. 13, 2017

(54) TOUCH PANEL SCANNING METHOD, CIRCUIT AND SYSTEM

(71) Applicant: STMicroelectronics Asia Pacific PTE LTD, Singapre (SG)

(72) Inventors: Dianbo Guo, Singapore (SG); Praveesh Chandran, Singapore (SG); Lokesh Kumar Korapati, Singapore (SG)

(73) Assignee: STMicroelectronics Asia Pacific Pte Ltd., Singapore (SG)

( * ) Notice: Subject to any disclaimer, the term of this patent is extended or adjusted under 35 U.S.C. 154(b) by 0 days.

(21) Appl. No.: 14/272,455

(22) Filed: May 7, 2014

(65) Prior Publication Data

US 2015/0324023 A1    Nov. 12, 2015

(51) Int. Cl.
*G06F 3/041*    (2006.01)
*A61B 17/22*    (2006.01)
*A61B 18/24*    (2006.01)
*A61B 18/26*    (2006.01)
*A61H 23/00*    (2006.01)
*G06F 3/044*    (2006.01)

(52) U.S. Cl.
CPC ...... *A61B 17/22022* (2013.01); *A61B 18/245* (2013.01); *A61B 18/26* (2013.01); *A61H 23/008* (2013.01); *G06F 3/044* (2013.01); *G06F 3/0416* (2013.01); *A61B 2017/22051* (2013.01); *A61B 2017/22079* (2013.01); *G06F 2203/04108* (2013.01)

(58) Field of Classification Search
CPC .... G06F 1/3262; G06F 3/0416; G06F 3/3265; G06F 3/044; G06F 2203/04104; G06F 3/041; G06F 3/0412
USPC ..................... 345/173–178; 178/18.01–20.04
See application file for complete search history.

(56) References Cited

U.S. PATENT DOCUMENTS

| | | | |
|---|---|---|---|
| 7,812,827 B2 | 10/2010 | Hotelling et al. | |
| 2013/0063390 A1* | 3/2013 | Kwon et al. | 345/174 |
| 2013/0194225 A1* | 8/2013 | Shen et al. | 345/174 |
| 2014/0098039 A1* | 4/2014 | Oda | 345/173 |
| 2014/0285465 A1* | 9/2014 | Hayashi et al. | 345/174 |

* cited by examiner

*Primary Examiner* — Amare Mengistu
*Assistant Examiner* — Stacy Khoo
(74) *Attorney, Agent, or Firm* — Seed IP Law Group LLP (57) ABSTRACT

A touch panel includes a plurality of drive lines, a plurality of orthogonal sense lines, and a plurality of sensors. A method of controlling the touch panel to detect touches includes simultaneously applying a drive signal to each of a group of drive lines of the touch panel. Each of the drive signals is applied to a corresponding drive line in the group during a time slot and all the applied drive signals having the same electrical characteristics over the time slot. The method includes sensing sense signals generated on the sense lines in response to the applied drive signals and processing the sense signals to detect touches of the touch panel.

17 Claims, 6 Drawing Sheets

| Time Slot | Sense Data on SL1 (i.e., SS1) |
|---|---|
| TS1 | $2C_{11}$ |
| TS2 | $C_{11} + C_{21}$ |
| TS3 | $C_{21} + C_{31}$ |
| TS4 | $C_{31} + C_{41}$ |
| ⋮ | |
| TS12 | $C_{111} + C_{121}$ |
| TS13 | $2C_{121}$ |

| Sum of Data obtained in Timeslots | Processed Raw Sense Data |
|---|---|
| TS1 and TS2 | $3C_{11} + C_{21}$ |
| TS2 and TS3 | $C_{11} + 2C_{21} + C_{31}$ |
| TS3 and TS4 | $C_{21} + 2C_{31} + C_{41}$ |
| TS4 and TS5 | $C_{31} + 2C_{41} + C_{51}$ |
| ⋮ | |
| TS12 and TS13 | $3C_{121} + C_{111}$ |
| | |

| Time Slot | Data obtained on S1 corresponds to |
|---|---|
| TS1 | Data 1 = $C_{11}$ |
| TS2 | Data 2 = $C_{11}$ + $C_{21}$ |
| TS3 | Data 3 = $C_{21}$ + $C_{31}$ |
| TS4 | Data 4 = $C_{31}$ + $C_{41}$ |
| ... | ... |
| TS12 | Data 12 = $C_{111}$ + $C_{121}$ |
| TS13 | Data 13 = $C_{121}$ |

800

| Data corresponding to Capacities | is given by |
|---|---|
| $C_{11}$ | Data 1 |
| $C_{21}$ | Data 2 - $C_{11}$ |
| $C_{31}$ | Data 3 - $C_{21}$ |
| $C_{41}$ | Data 4 - $C_{31}$ |
| $C_{51}$ | Data 5 - $C_{41}$ |
| ... | ... |
| $C_{121}$ | Data 13 |

802

| Data corresponding to Capacities | is given by |
|---|---|
| $C_{11}$ | Data 1 |
| $C_{21}$ | Data 2 - $C_{31}$ |
| $C_{31}$ | Data 3 - $C_{41}$ |
| ... | ... |
| $C_{101}$ | Data 11 - $C_{111}$ |
| $C_{111}$ | Data 12 - $C_{121}$ |
| $C_{121}$ | Data 13 |

TOUCH PANEL SCANNING METHOD, CIRCUIT AND SYSTEM

TECHNICAL FIELD

The present disclosure relates generally to touch panels and more specifically to methods, circuits, and systems for scanning drive and sense lines of a touch panel to detect touch and hover events.

BACKGROUND

Touch screens are present in many different types of common modern electronic devices, such as smart phones, tablet computers, portable music and video devices, personal digital assistants, portable gaming devices, computer systems, and so on. In these electronic devices the touch screen is part of the user interface of the device. The touch screen typically includes a visual display and touch sensors or a touch panel. A touch controller is coupled to the touch screen and operates to process signals from the touch panel to detect inputs by a user. The touch panel includes some sort of transparent sensor array, such as an ultrasonic, resistive, vibration or capacitive sensor array, or a combination thereof, which is attached to or formed as an integral part of the visual display, which may be a liquid crystal display (LCD), for example.

In operation, a user touches a surface of touch panel or "hovers" his or her finger or a suitable object above the touch panel, and the sensor array generates corresponding electronic sensor signals that are provided to the touch controller. From these sensor signals, the touch controller determines the type of "touch event" or "hover event" input by the user to the touch panel and provides this information to processing circuitry in the electronic device. The processing circuitry operates in response to this information to allow a user to control the electronic device or an application running on the processing circuitry through these touches of the touch panel. Many current touch panels are capable of detecting multiple touch and hover events simultaneously, and may also detect gesture events that are similar to hover events except involve a predefined motion of a user's finger.

A typical sensor array of a touch panel is a capacitive sensor array including a number of force or drive lines and orthogonally arranged sense lines. These lines are made from suitable conductive materials, such as Indium Tin Oxide (ITO), which are transparent to visible light. In the touch panel, the drive lines are formed on one layer of the sensor array structure and the sense lines formed on another layer of the structure, with these layers being separated by a transparent insulating material such as glass. The overlap of the drive lines and the orthogonally arranged sense lines with the insulating material between forms an array of capacitive sensor nodes or sensors. In operation, a drive signal, which is typically a periodic waveform such as a pulse train, is applied successively to the drive lines. As the drive signal is applied to a given drive line, the capacitive coupling between that drive line and the sense lines through the corresponding sensor nodes results in capacitive coupling of the drive signal to the sense lines to thereby generate sense signals on the sense lines responsive to the drive signal.

The value of the sense signal generated on each sense line is a function of the capacitive coupling between that sense line and the drive line receiving the drive signal. This capacitive coupling changes in response to a user's finger, or other touch device, being proximate the sensor nodes formed at the overlap of the drive and sense lines. This change in capacitive coupling of the drive signal to the sense lines will result in a change in the sense signal generated on the sense lines, and in this way the sense signals indicate whether a user's finger or other touch device is adjacent a given sensor node in the touch panel.

In operation, to scan the entire sensor array of a touch panel the drive signal must be applied to each drive line and the resulting sensor signals on the sensor lines sensed and processed to detect touch or hover events. As a result, the time it takes to scan the entire sensor array is function of the number of sensors in the array. A response time is determined by the time it takes to scan an array and process the corresponding sense signals to detect touch and hover events on the touch panel. If the response time of a touch panel is too slow this will manifest itself as an unpleasant experience for the user of the electronic device containing the touch panel. The user will notice undesirable delays between inputting a touch or hover input and the electronic device responding to this input. The size of a touch panel is the number of sensors in the touch panel and as the size increases the response time typically increases. This is true because a larger size touch panel has more sensors and thus more drive and sense lines to control. As a result, a method of scanning a touch panel having a given size suitable for an electronic device such as a smart phone may be unsuitable for larger size touch panels in devices such as tablet computers, notebook computers, and televisions. Accordingly, there is a need for improving the way in which touch panels are scanned to ensure the response times of the touch panels are acceptable for desirable operation of the associated electronic device.

SUMMARY

In one embodiment of the present disclosure, a touch panel includes a plurality of drive lines, a plurality of orthogonal sense lines, and a plurality of sensors. A method of controlling the touch panel to detect touches includes simultaneously applying a drive signal to each of a group of drive lines of the touch panel. Each of the drive signals is applied to a corresponding drive line in the group during a time slot and all the applied drive signals having the same electrical characteristics over the time slot. The method includes sensing sense signals generated on the sense lines in response to the applied drive signals and processing the sense signals to detect touches of the touch panel.

DETAILED DESCRIPTION

Figure 1:
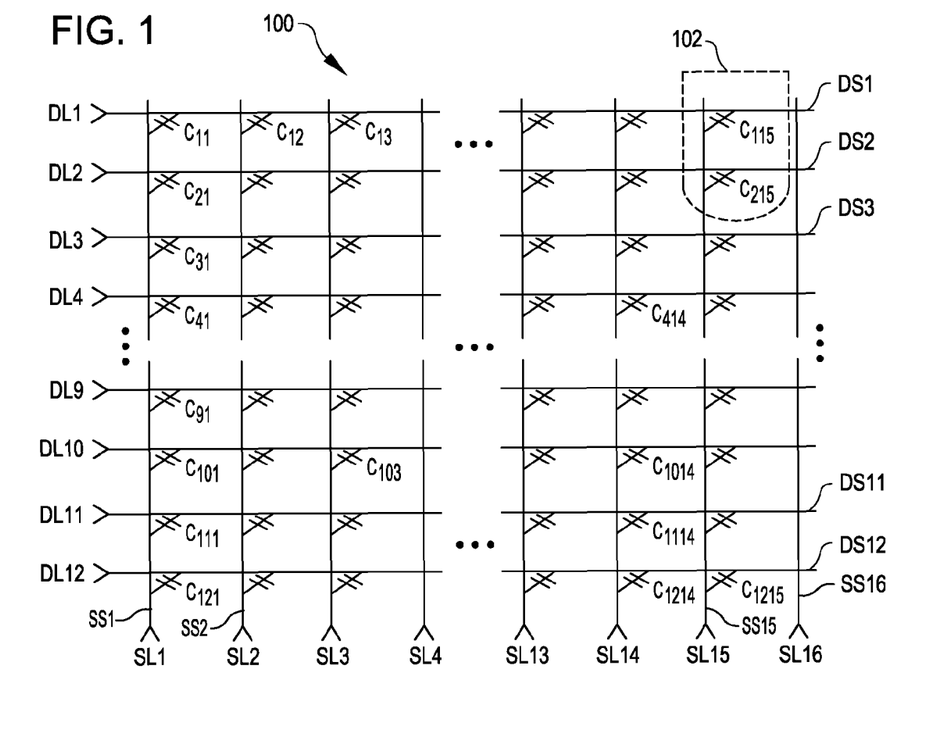
FIG. 1 is a functional diagram illustrating a touch panel including capacitive sensor nodes, drive lines, and sense lines.

FIG. 1 is a functional diagram illustrating a touch panel 100 including a number of drive lines DL and sense lines SL, with a capacitive sensor node or sensor $C_{nm}$ being formed at the overlap of each drive line and sense line, as previously discussed. In the example of FIG. 1, the touch panel 100 includes a total of N drive lines, where N=12, and thus the touch panel includes drive lines DL1-DL12. The touch panel 100 also includes a total of M sense lines, where M=16 and so the touch panel includes sense lines SL1-SL16. The capacitive sensors $C_{nm}$ are formed at the overlap of the 16 sense lines SL and the 12 drive lines DL and there are accordingly 192 sensors $C_{nm}$ in the touch panel 100. The subscript n indicates the drive line DL associated with the capacitive sensor $C_{nm}$ so n=(1-N) in the example of FIG. 1. The subscript m indicates the sense line SL associated with a capacitive sensor $C_{nm}$ and m=(1-M). Selected capacitive sensors $C_{nm}$ are labeled in FIG. 1 as examples of notation being utilized to identify each sensor in the array of sensors $C_{nm}$ in the touch panel 100. According to embodiments of the present disclosure, multiple drive lines DL are simultaneously driven or activated with drive signals DS having the same electrical characteristics, and the resulting sense signals SS generated on the sense lines SL are then sensed and processed to detect the presence of touches on the touch panel 100, as will be explained in more detail below.

In the following description, certain details are set forth in conjunction with the described embodiments of the present disclosure to provide a sufficient understanding of the present disclosure. One skilled in the art will appreciate, however, that embodiments of the disclosure may be practiced without these particular details. Furthermore, one skilled in the art will appreciate that the example embodiments described below do not limit the scope of the present disclosure to only these embodiments, and will also understand various modifications, equivalents, and combinations of the disclosed embodiments and components of such embodiments that are also within the scope of the present disclosure. Embodiments including fewer than all the components of any of the respective described embodiments may also be within the scope of the present disclosure although not expressly described in detail below. Finally, the operation of well-known components and/or processes has not been shown or described in detail below to avoid unnecessarily obscuring the present disclosure. Also note that in the present description when referring generally to any one of the capacitive sensors $C_{nm}$ drive lines DL1-12, and sense lines SL1-16 the subscript or number designation may be omitted. Only when referring to a specific one of these components will specific subscripts or number designations be included. In addition, the description of the disclosed embodiments of the present disclosure utilizes the terms "touch" or "touches" to refer to any type of user input event that is sensed by the touch panel 100.

FIG. 1 illustrates a user's finger 102 applying a touch in the upper right hand portion of the touch panel 100. The finger 102 is large enough that the finger covers more than one capacitive sensor $C_{nm}$ when touching the touch panel 100. In the example of FIG. 1, the finger 102 touches the capacitive sensors C115 and C215. As a result, a sense signal SS generated on the sense line SL15 in response to drive signals DS applied on the drive lines DL1 and DL2 will have values indicating the variation in the capacitance values of the sensors C115 and C215 and thus indicating a touch occurring at these capacitive sensors. The drives signals DS applied to the drives lines DL1-DL12 are designated DS1-DS12, respectively, while the sense signals SS generated on the sense lines SL1-SL16 are designated SS1-SS16, respectively.

Figure 2:
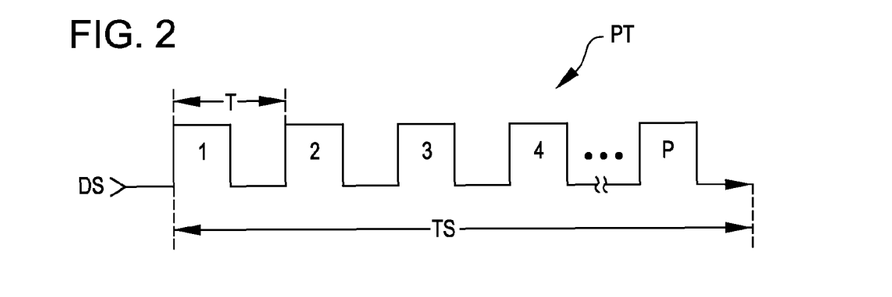
FIG. 2 is signal timing diagram showing a series of pulses or "pulse train" corresponding to the drive signal applied to each of the drive lines of the touch panel of FIG. 1 during scanning of the touch panel.

The operation of the touch panel 100 in detecting a touch, such as the touch of the finger 102, will now be described in more detail with reference to FIGS. 2 and 3. In operation, a touch controller (not shown in FIG. 1) sequentially applies a drive signal DS to the drive lines DL1-DL12 and senses the sense signals SS generated on the sense lines SL1-SL16 in response to each of these drive signals. Typically, the drive signal DS applied to each of the drive lines DL is a series of pulses or a "pulse train" (PT) as illustrated in FIG. 2. The pulse train PT includes a series of pulses a labeled 1-P, where P is a number defining the total number of pulses that are applied during a time slot TS of the drive signal. The time slot TS defines the entire duration for which the drive signal DS is applied to each drive line DL. Each pulse 1-P has a period T so the time slot TS=(P=T).

Figure 3:
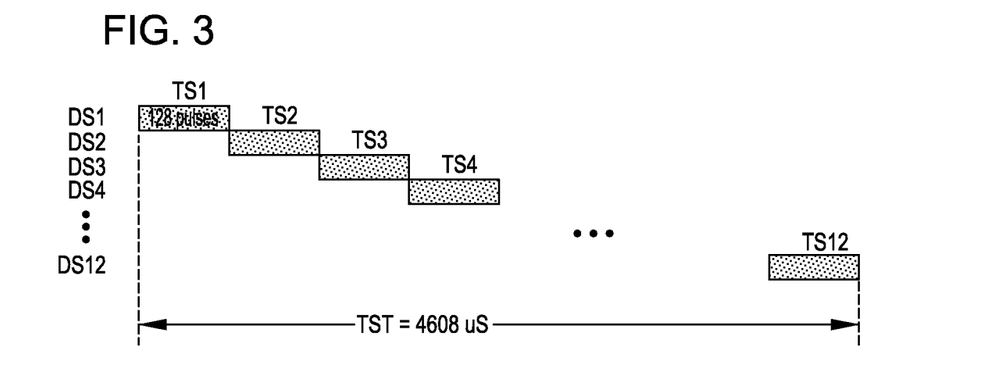
FIG. 3 is a diagram illustrating a conventional method of activating the drive lines of the touch panel of FIG. 1 to detect touches.

Referring now to FIG. 3, to scan the entire touch panel 100 the touch controller (not shown) sequentially applies the drive signal DS to each of the drive lines DL1-DL12 in a respective time slot TS. As discussed above and shown in FIG. 2, a time slot TS corresponds to the duration for which the drive signal DS is applied to each drive line DL. Thus, as shown in FIG. 3, the touch controller (not shown) initially applies the drive signal DS1 to drive line DL1 in a first time slot TS, which is designated TS1. During this first time slot TS1, the touch controller also senses the sense signals SS1-SS16 (FIG. 1) generated on the sense lines SL1-SL16 in response the DS1 signal. The touch controller then applies the drive signal DS2 to the drive line DL2 in a second time slot TS designated TS2 and senses the sense signals SS1-SS16 generated on the sense lines SL1-SL16 in response the DS2 signal. The touch controller continues sequentially applying the drive signals DS in this way and sensing sense signals SS generated in response to each drive signal during each of the time slots TS3-TS11. Finally, the drive signal DS12 is applied to the drive line DL12 in a twelfth time slot TS12 and the sense signals SS1-SS16 during this twelfth time slot are sensed, which completes the sensing of the sensors $C_{nm}$ of the entire touch panel 100. This sensing of all the sensors $C_{nm}$ is referred to as a "scan" of the touch panel 100.

The detailed operation regarding the manner in which the sense signals SS1-SS16 are generated responsive to the applied drive signals DS will be understood by those skilled in the art, and thus, for the sake of brevity, will not be described in detail herein. Briefly, the drive signal DS applied to a given drive line DL is capacitively coupled through the capacitive sensors $C_{nm}$ to the sense lines SL. The amount of capacitive coupling from the drive lines DL to the sense lines SL depends on the values of the capacitive sensors $C_{nm}$, each of which depends on the presence or absence of a touch or hover event proximate the sensor. The value of the capacitive sensor $C_{nm}$ thus determines the amount of charge that is transferred to sense line SL responsive to each pulse of the drive signal DS (see FIG. 2). This charge transfer is typically integrated over the time slot TS during which the drive signal DS is applied to a given drive line DL to thereby generate a voltage having a value that indicates whether a touch is present or not.

The signal generated on the sense line SL due to this charge transfer is the sense signal SS. The value of each capacitive sensor Cnm is reduced by the presence of a touch and thus the capacitive coupling between the drive line DL and sense line SL is lower when a touch is present. As a result, the value of the voltage after integration of the sense signal SS over the time slot TS has a smaller value when a touch is present (i.e., a smaller value of Cnm and thus smaller charge transfer responsive to each pulse of the drive signal DS). The voltage has a larger value when a touch is not present (i.e., a larger value of Cnm and thus more charge transfer each pulse of the drive signal DS). Thus, when the voltage is greater than some threshold value the touch controller determines no touch is present at the sensor Cnm and when the voltage is less than this threshold value a touch is determined to be present. The touch controller may process the voltage generated from the sense signal SS in a variety of different ways in determining whether a touch has occurred, as will be appreciated by those skilled in the art. This processing may include, for example, analog-to-digital (A/D) conversion, baseline subtraction, low pass filtering, and so on, as will be appreciated by those skilled in the art.

Returning now to FIG. 3, after the scan of the touch panel 100 the touch controller processes the sense signals SS1-SS16 generated during each of the time slots TS1-TS12 to detect the presence of a touch or touches on the touch panel, such as the finger 102 in FIG. 1. Sequentially applying a single drive signal DS to each of the drive lines DL1-DL12 as illustrated in FIG. 3 is a conventional way of controlling or scanning a touch panel. In this approach, when the pulse train PT (FIG. 2) that is applied to a drive line DL includes 128 pulses and each pulse has a period T=3 µS, the response time, namely the time to scan the entire touch panel 100 (FIG. 1) including twelve drive lines DL1-DL12 is given by (12×128×3 µS)=4608 µS or 4.6 ms, which is indicated in FIG. 3. This ignores any processing time required by the touch controller after a scan but is used herein to show the effect of the scan time on the response time. A response time of 4.6 ms may be acceptable and can be achieved for a 12×16 touch panel 100 (i.e., twelve drive lines DL and sixteen sense lines SL) as just described.

When the touch panel 100 is larger, however, and includes more drive lines DL the resulting response time may be too slow to be acceptable. For example, a typical response time requirement is 100 Hz, meaning the touch controller must report the presence and location of a touch every 10 ms. Half of this time may be required to detect a touch input by the user and the other half required to detect other types of user inputs, such as hover inputs. Accordingly, for larger touch panels 100, as are used in electronic devices having larger visual displays such as laptop computers, tablet computers, televisions, and so on, the increased number of drive lines DL and resulting increased scan time may result in an unacceptable slow response time with the scanning approach of FIG. 3.

In an attempt to lower the scan time, the period T of pulses of the drive signal DS applied to each drive line DL in each time slot TS could be reduced. Fewer, shorter period T and thus higher frequency pulses could in theory be used as the drive signals DS to lower the scan time of the touch panel 100. There are, however, limits to this approach, as will be appreciated by those skilled in the art. In general, the electrical characteristics of a touch panel determine the characteristics of the drive signals DS that are applied to that touch panel. For example, the lengths and widths of the indium tin oxide (ITO), or other material, lines forming the drive lines and sense lines have capacitances and resistances determined by the physical size and layout of these lines. These electrical characteristics are one factor that determines the electrical characteristics of the drive signals DS applied to the touch panel.

Another way in which the scan time of a touch panel could in theory be reduced is by reducing the number of pulses of the drive signal DS applied to the drive lines DL during each time slot TS. In other words, the duration of the time slots TS could be reduced to thereby reduce the overall scan time of the touch panel. Once again, there are practical limits, determined at least in part by the physical characteristics of the touch panel, as to the minimum number of pulses that may be utilized. The fewer the number of pulses of the drive signal DS applied during a time slot TS the smaller will be the integrated voltage generated in response to the corresponding sense signals SS. As a result, the fewer the number of pulses the more susceptible to "noise" are the integrated voltages. As a result, a sufficient number of pulses for the drive signals DS is utilized so that a reliable average value is generated for the integrated voltage, reducing the effect of noise. Each capacitive sensor Cnm in a typical touch panel has a value on the order of 1-2 picofarads (pF) and the change in this capacitance value due to a touch is typically on the order of 0.1 pF. With such small capacitances ambient noise can certainly affect the values of the capacitive sensors Cnm and thus a sufficient number of pulses for the drive signal DS must be utilized so that a reliable average value for the integrated voltage is generated notwithstanding such ambient noise. For example, if only two pulses were utilized for each drive signal DS during a time slot TS and one of these pulses was affected by ambient noise the resulting integrated voltage could be greatly affected. In contrast, where 128 pulses are utilized for each drive signal DS and one of these pulses is affected by ambient noise the resulting integrated voltage would be minimally affected.

Figure 4:
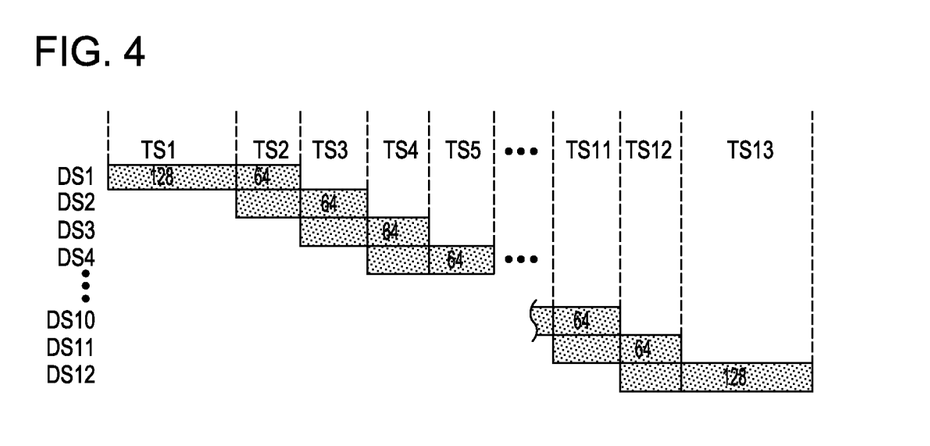
FIG. 4 is a diagram illustrating a method of activating the drive lines in a touch panel to detect touches according to one embodiment of the present disclosure.

FIG. 4 is a diagram illustrating a method of activating the drive lines DL in a touch panel to detect touches according to one embodiment of the present disclosure. In the approach of FIG. 4, a first drive line DL1 and last drive line DL12 have the drive signal DS applied individually to these drive lines in first and last time slots TS but all other drive lines DL2-DL11 have the drive signals DS applied to pairs of the drive lines, as will now be explained in more detail. In the present description, a drive line DL may be said to be "activated" to mean that the drive signal DS is applied to that drive line.

Figure 5:
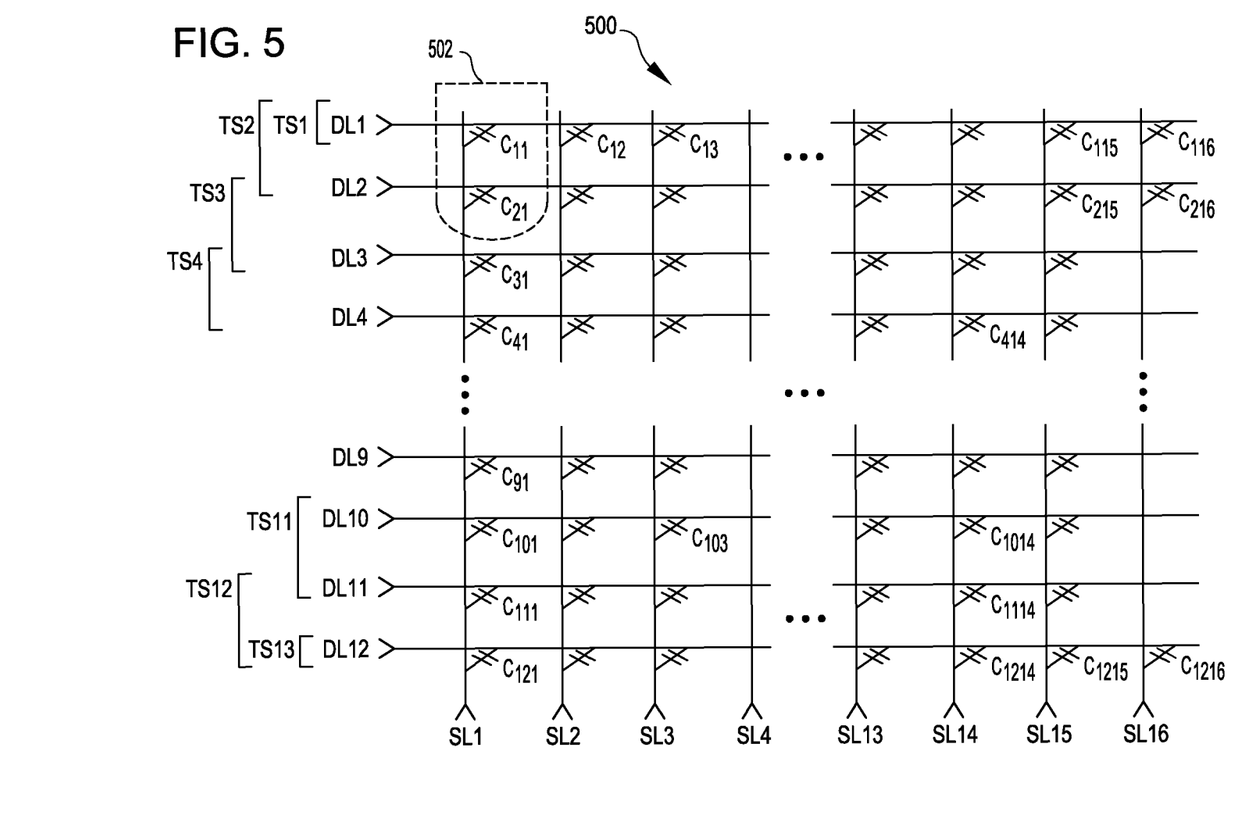
FIG. 5 is a diagram of a touch panel illustrating the method of FIG. 4 in scanning the touch panel.

The overall process illustrated in FIG. 4 will now be described in more detail with reference to FIGS. 4 and 5, where FIG. 5 illustrates a touch panel 500 that is controlled or scanned according to the process of FIG. 4. The touch panel 500 is the same as the touch panel 100 of FIG. 1 and thus includes 12 drive lines DL1-DL12 and sixteen sense lines SL1-SL16. In the embodiment of FIGS. 4 and 5, in a first time slot TS1 a touch controller (not shown) applies a drive signal DS1 only to the drive line DL1 (FIG. 1) and includes 128 pulses (i.e., P=128 in FIG. 2). This is indicated through the number "128" in the rectangle for the first drive signal DS1 during the first time slot TS1 in FIG. 4. This is also illustrated in FIG. 5 through the left square bracket around the first drive line DL1 and the time slot TS1 label to the left of this bracket, indicating that during the first time slot TS1 the drive signal DS1 is applied to the first drive line DL1. During the first time slot TS1 the touch controller senses the sense signals SS1-SS16 generated on the sense lines SL1-SL16 responsive to the applied first drive signal DS1.

After the termination of the first time slot TS1, the touch controller applies the drive signal DS1 to the first drive line DL1 and at the same time applies a second drive signal DS2 to the second drive line DL2 during a second time slot TS2. Each of the drive signals DS1 and DS2 during the second time slot TS2 is a pulse train of only 64 pulses (P=64 in FIG. 2) as indicated through the number 64 shown in the rectangle in FIG. 4 during the second time slot. Accordingly, the second time slot TS2 need only be half as long as the first time slot TS1 since the applied drive signals DS1, DS2 include only half the number of pulses as the drive signal DS1 during the first time slot TS1. This application of the drive signals DS1, DS2 to the drive lines DL 1, DL 2 during the second time slot TS2 is illustrated again with a left square bracket adjacent the drive lines DL1, DL2 and the label TS2 in FIG. 5. During the second time slot TS2 once again the touch controller senses the sense signals SS1-SS16 generated on the sense lines SL1-SL16 responsive to the applied first and second drive signals DS1 and DS2 on the drive lines DL1 and DL2. As a result of the drive signals DS1 and DS2 being simultaneously applied to the drive lines DL1 and DL2 during the second time slot TS2, the resulting sense signals SS1-SS16 will contain information about the sensors $C_{11}$-$C_{116}$ associated with the first drive line DL1 as well as information about the sensors $C_{21}$-$C_{216}$ associated with the second drive line DL2, as will be described in more detail below with reference to FIG. 6.

In the process of FIG. 4 the touch controller continues operating as just described for the second time slot TS2 in subsequent consecutive time slots TS2, TS3, and so on, activating or applying drive signals DS of 64 pulses to adjacent drive lines DL. For example, during the time slot TS3 the controller activates the drive lines DS2 and DS3, in the time slot TS4 the controller activates the drive lines DS3 and DS4, and so on until during a twelfth time slot TS12 the controller activates the drive lines DS11 and DS12 as seen in FIG. 4. The touch controller senses the generated sense signals SS1-SS16 during each of these time slots TS3-TS12. Finally, the touch controller applies the drive signal DS12 to only the drive line DL12 during a thirteenth time slot TS13, with this drive signal being 128 pulses (P=128 in FIG. 2) just as was the case for the drive signal DS1 during the first time slot TS1. Once again, the touch controller senses the generated sense signals SS1-SS16 during the thirteenth time slot TS13. The left square brackets and time slot TS labels in FIG. 5 also illustrates these process operations.

Figure 6:
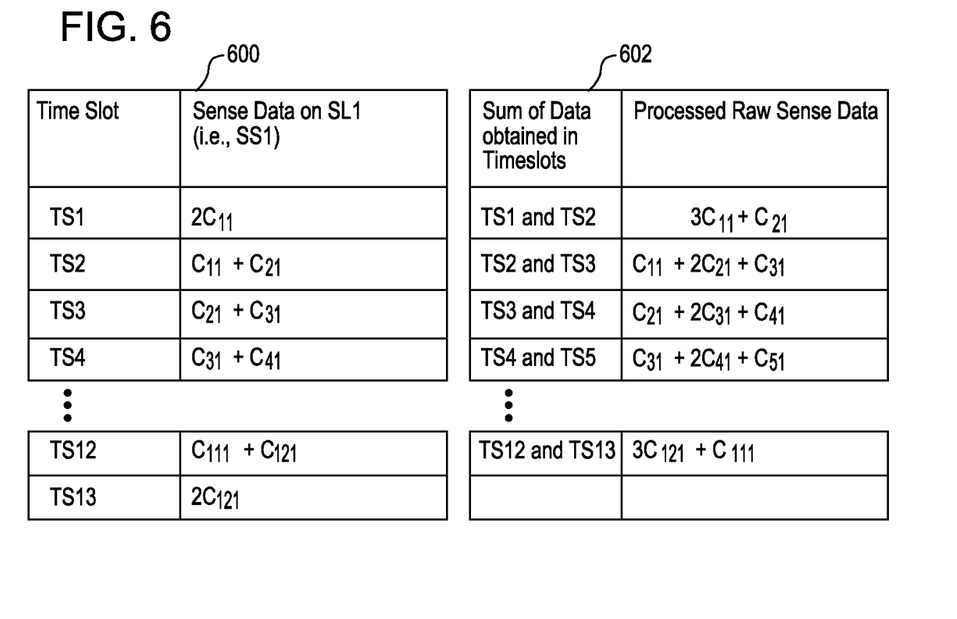
FIG. 6 contains two tables illustrating the raw sense data or signals captured in respective time slots for one of the sense lines and the processing of this raw sense data to detect touches according to the method of FIGS. 4 and 5.

The resulting sense data, namely the sense signals generated by the process of FIGS. 4 and 5, and the processing of this sense data to detect touches, such as the touch generated by a finger 502 in FIG. 5, will now be described in more detail with reference to FIG. 6. FIG. 6 contains two tables, a first table 600 illustrating the raw sense data captured in respective time slots TS1-TS13 for the sense lines SL1, and a second table 602 showing the processing of this sense data to detect a touch according to the method of FIGS. 4 and 5. As seen in table 600, in the first time slot TS1 the sense data or sense signal SS1 captured by the touch controller indicates twice the value of the capacitive sensor C11. Note the terms sense data and sense signal are used interchangeably in the present description.

The sense signal SS1 indicates two times the value of the capacitance of the capacitive sensor C11 in the first time slot TS1 because this time slot is twice as long and includes twice as many pulses (i.e. 128 pulses versus 64 pulses) as the other time slots TS2-TS12. The value of the capacitive sensor $C_{11}$ determines the amount of charge that is transferred to the sense line SL1 responsive to each pulse of the drive signal DS1 and, as described above, this charge transfer is integrated over the time slot TS1 during which the drive signal DS is applied to the drive line DL1. This integration generates a voltage having a value that indicates the value of the capacitive sensor C11 and in this way indicates whether a touch is present at the sensor C11. The integration voltage generated during a time slot is proportional to the number of pulses contained in the drive signal DS during that time slot. As a result, the integration voltage during the first time slot TS1 will have twice the amplitude or value as voltages generated during the time slots TS2-TS12 because the drive signal DS1 includes 128 pulses during the time slot TS1 and all the other drive signals DS2-DS11 include only 64 pulses. Thus, the sense data or the sense signal during the first time slot TS1 will indicate twice the value of the capacitive sensor C11, which is illustrated in the first row of the table 600. So in the first row of table 600 the "2C11" in the right column indicates that the integrated voltage generated from the sense signal SS1 during the time slot TS1 has an amplitude indicating twice the value of the capacitive sensor C11 because the amplitude is double the amplitude for integrated voltages generated from the sense signal SS1 in the time slots TS2-TS12 where the drive signal DS1 includes only 64 pulses.

As seen in the second row of the table 600, the integrated voltage generated from the sense data or sense signal SS1 during the second time slot TS2 indicates the values of the capacitive sensors C11 and C21 (i.e., C11+C21). This is true because as seen in referring back to FIGS. 4 and 5, both the drive signal DS1 and the drive signal DS2 are applied to the corresponding drive lines DL1 and DL2 during the second time slot. The same is true for each of the subsequent time slots TS3-TS12 as seen in table 600, with the sense signal SS1 captured during each of these time slots indicating the values for the two capacitive sensors Cn1 associated with the activated drive lines DL during that time slot. Thus, for the third time slot TS3 the sense signal SS1 indicates the values of the capacitive sensors C21 and C31 (C21+C31), while the sense signal indicates the values of the capacitive sensors C31 and C41 (C31+C41) in the fourth time slot TS4, and so on, with the sense signal indicating the values of the capacitive sensors C111 and C121 (C111+C121) in the twelfth time slot TS12. Finally, in the thirteenth time slot TS13 the sense signal SS1 indicates twice the value of the capacitive sensor C121 for the same reasons as discussed in detail above with regard to the first time slot TS1 because the drive signal DS12 during the thirteenth time slot also includes 128 pulses (see FIG. 4).

From the raw sense data in table 600 formed by the captured sense signal SS1 during the time slots TS1-TS13, the touch controller processes this raw sense data as illustrated in table 602 to detect the presence of a touch, such as the touch generated by the finger 502 in FIG. 5. In this embodiment, the processing of the raw sense data corresponds to summing the sense data from adjacent time slots TS to thereby generate processed sense data as seen in the right column of table 602 having values that indicate whether a touch has occurred or not for a given capacitive sensor C11-C121. In this way, the processed sense data from the time slots TS1 and TS2 indicates whether a touch is occurring at the capacitive sensor C11, the processed sense data from the time slots TS2 and TS3 indicates whether a touch is occurring at the capacitive sensor C21, the processed sense data from the time slots TS3 and TS4 indicates whether a touch is occurring at the capacitive sensor C31, and so on, with the processed sense data from the time slots TS12 and TS13 indicating whether a touch is occurring at the capacitive sensor C121. The raw sense signals SS2-SS16 captured for the sense lines SL2-SL16 are processed in the same way as described with reference to FIG. 6 for the sense line SS1, and thus, for the sake of brevity, the generation of the processed sense data for the sense lines SL2-SL16 will not be described in more detail.

The processed sense data in the table 602 indicates that a touch has occurred or not for a corresponding single capacitive sensor Cnm since the contribution from one capacitive sensor in each time slot TS is greater than the contribution from the other capacitive sensors in that time slot. For example, the first row of table 602 indicates the summation of the sense signal SS1 for the time slots TS1 and TS2 and thus has a value (3C11+C21). Accordingly, this summed value is predominantly determined by the value of the capacitive sensor C11 and can therefore be utilized to determine whether a touch has occurred at the capacitive sensor C11. Similarly, the summation of the sense signal SS1 for the time slots TS2 and TS3 has a value (C11+2C21+ C31) and this summed value is predominantly determined by the value of the capacitive sensor C21. Thus, this summed value can be utilized to determine whether a touch has occurred at the capacitive sensor C21. The same is true for the remaining summed values in the table 602.

With the method of FIGS. 4-6, the number of pulses 128 for the drive signal DS1 during the first time slot TS1 and the last time slot TS13 is double the number of pulses 64 for the drive signal DS1 in the intervening time slots TS2-TS12. This is done so that the amplitude of summed values for the processed sense data is approximately the same for each of the summed voltage values generated as shown in table 602. More specifically, the amplitude of each of the summed values in table 602 is four times the amplitude for a given capacitive sensor Cn1 when 64 pulses are applied as the drive signal. So in the first row, ignoring the capacitive sensors Cn1 involved, the amplitude is (3+1)=4, in the second row the amplitude is similarly (1+2+1)=4, and so on for all the summed voltage values in this table. This would not be true for the first and last summed values in the table 602 if the drive signal DS1 was only 64 pulses in time slots TS1 and TS13.

The method of FIGS. 4-6 significantly reduces the amount of time required to scan the touch panel 500. The touch panel 500 is the same size as the touch panel 100 of FIG. 1 and with the conventional scanning method described with reference to FIG. 3 the scan time was 4.6 ms as discussed above. In contrast, the method in the embodiment of FIGS. 4-6 requires a scan time of (128 pulses×3 uS/pulse)×2 for the time slots TS1 and TS3, plus (64 pulses×3 uS/pulse)×11 for the time slots TS2-TS12, which is equal to 2880 µS or 2.88 ms. This is a 37.5% reduction in the scan time relative to the method of FIG. 3.

In methods of activating the drive lines DL in a touch panel according to other embodiments of the present disclosure, instead of activating pairs of drive lines simultaneously, as in the embodiment just described with reference to FIGS. 4-6, groups of drive lines DL are simultaneously activated where each group includes three or more drive lines to which drive signals are simultaneously applied. In such embodiments, multiple drive lines DL are simultaneously driven or activated with drive signals DS having the same electrical characteristics, where the multiple drive lines include three or more drive lines. The electrical characteristics of the drive signals DS that are the same include the frequency and phase of the drive signals.

Figure 7:
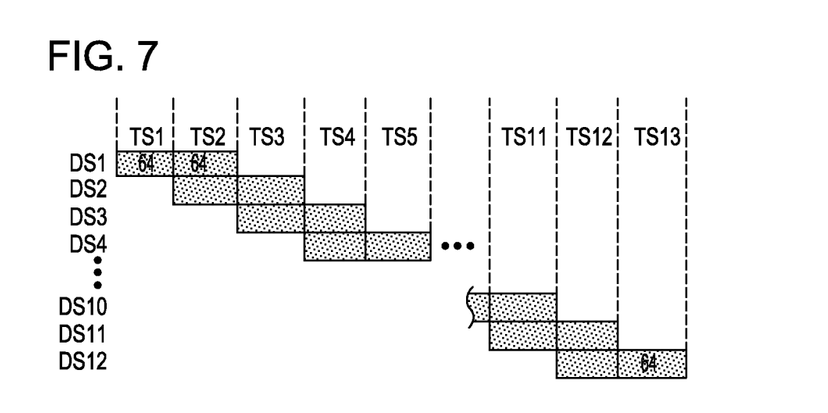
FIG. 7 is a diagram illustrating a method of activating the drive lines in the touch panel of FIG. 5 to detect touches according to another embodiment of the present disclosure.

FIG. 7 is a diagram illustrating a method of activating the drive lines DL in the touch panel 500 of FIG. 5 to detect touches according to another embodiment of the present disclosure. In the embodiment of FIG. 7, the method is the same as the method of FIG. 4 except that in the first time slot TS1 and final time slot TS13 the applied drive signal DS1 includes only 64 pulses and not 128 pulses as was the case in the embodiment of FIG. 4. As a result, the method of FIG. 7 will not be described in great detail since it will be understood as a variation in the number of pulses for the drive signal DS1 in the first and the last time slots TS1, TS13 relative to the method previously described in detail with reference to FIGS. 4 and 5.

Figure 8:
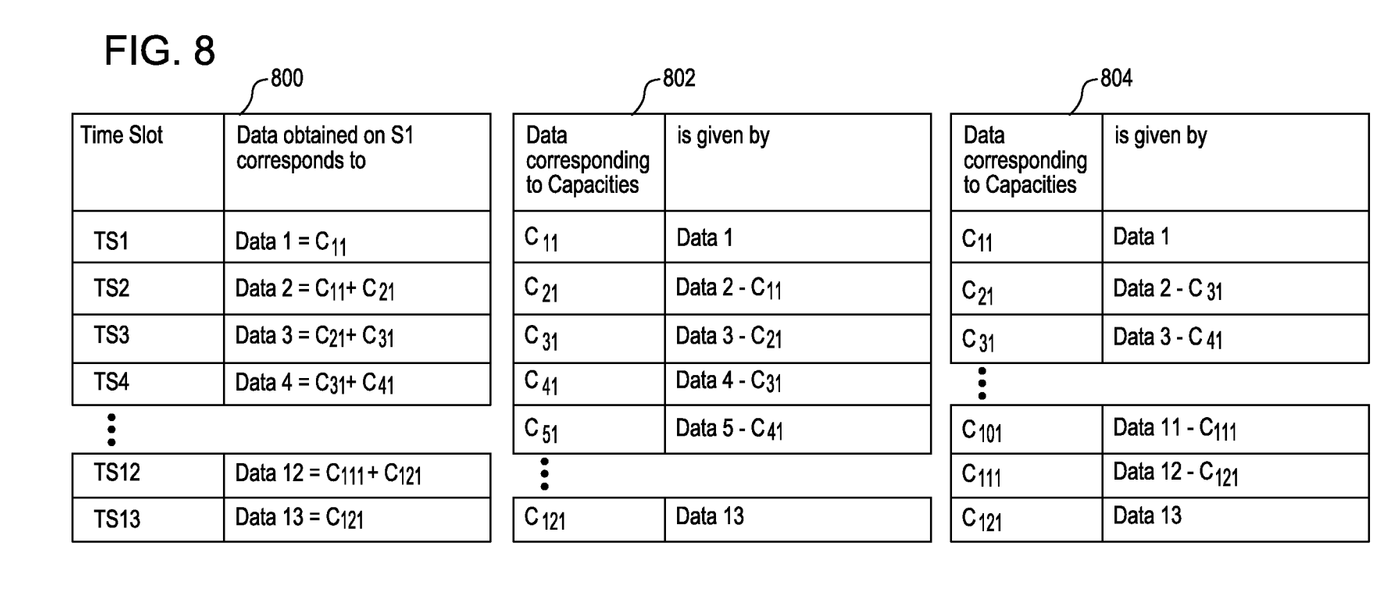
FIG. 8 is a table illustrating the raw and processed sense data captured in respective time slots for one of the sense lines according to the method of FIG. 7.

FIG. 8 is a table illustrating the raw sense data generated by the method of FIG. 7 in a table 800 and showing two different ways of processing this raw sense data in tables 802 and 804 according to respective embodiments of the present disclosure. In the table 800, the raw sense data or send signal SS1 for each timeslot TS1-TS13 is designated as Data1-Data13, respectively. As seen in the first row of table 800, the raw sense data or sense signal SS1 generated during the first time slot TS1 indicates the value of the capacitive sensor C11. More specifically, as discussed above in more detail with reference to FIGS. 4-6, the integrated voltage resulting from the sense signal SS1 over the first time slot TS1 indicates the value of the capacitive sensor C11, which is designated Data1. During the second time slot TS2, the drive signal DS is applied to both driveline DL1 and DL2 so that the integrated voltage resulting from the corresponding sense signal SS1 indicates the values of the capacitive sensors C11 and C21 (C11+C21), with this sum being designated Data2 in table 800. The rows two through twelve of the table 800 for the time slots TS2-TS12 each contain a corresponding sum of capacitive sensor Cnm values, meaning the integrated voltage generated during each of those timeslots indicates the values of the corresponding pair of capacitive sensors Cnm. Finally, in the last row of the table 800 the integrated voltage resulting from the sense signal SS1 over the last time slot TS13 indicates the value of the capacitive sensor C121, which is designated Data13.

A first embodiment of a method for processing the raw sense data in the table 800 to detect touches is illustrated in table 802 and is referred to as a forward-subtraction method herein. The left column in the table 802 indicates the capacitive sensor C11-C121 whose value is given by the processed raw sense data in the right column of the table and in the same row. Thus, in row one of the table 802 the value of the capacitive sensor C11 is given by Data1, which is seen from table 800 correspond to the integrated voltage generated during the first timeslot TS1. The second row of the table 802 indicates the value of the capacitive sensor C21 is given by (Data2−C11) or (C11+C21−C11)=C21. Similarly, the third row of the table 802 indicates the value of the capacitive sensor C31 is given by (Data3−C21) or (C21+C31−C21)=C31. Thus, the method continues in this way subtracting the determined values for capacitive sensors Cnm from raw sense data to generate the processed sensor data indicating the value for the next capacitive sensor to thereby determine values for the sensors C41-C111. Finally, the value of the capacitive sensor C121 is given by Data13 determined in the time slot TS13 in which only the drive line DL12 was activated, just as for the drive line DL1 in time slot TS1, as is seen by referring back to FIG. 7.

The method illustrated by table 802 is termed a "forward subtraction" method because the value of the first capacitive sensor C11 is first determined, and this value is then forwarded for use in determining the value of the next capacitive sensor C21. This is seen in row two of the table 802 where the determined value for the sensor C11 determined in time slot TS1 is subtracted from the raw sense data Data2 determined in time slot TS2 to thereby determine the value of the capacitive sensor C21. Next, in row three of the table 802 the value for the sensor C21 just determined in row two is now forwarded and subtracted from the raw sense data Data3 determined in time slot TS3 to determine the value of the capacitive sensor C31. In row four of the table 802 the value for the sensor C31 just determined in row three is now forwarded and subtracted from the raw sense data Data4 determined in time slot TS4 to determine the value of the capacitive sensor C41. Thus, with this method, starting with the value for the capacitive sensor C11 determined in time slot TS1, the value of the next capacitive sensor Cnm is determined using the raw sense data from the next time slot TS. This is done until the final time slot TS13 during which only the drive line DL12 was activated so the sense signal SS1 generated during the thirteenth time slot indicates the value of the capacitive sensor C121 without any subtraction being necessary, as was the case for time slot TS1.

After processing the raw sense data in table 800 according to the forward subtraction method illustrated in table 802, the values for all the capacitive sensors C11-C121 have been generated and the touch controller may determine whether any of these values indicate a touch is occurring at that sensor. For example, in FIG. 5 the finger 502 is touching the touch panel 500 at the sensors C11, C21 and the integrated voltage values generated for these sensors according to the forward subtraction method of table 802 would thus indicate a touch is occurring at these sensors.

The method illustrated by table 804 is similar to that just described for table 802, but operates in the reverse direction and is thus termed a "backward-subtraction" method. Instead of starting with the value for the first capacitive sensor C11, the method of table 804 starts with the value for the last capacitive sensor C121. As seen in the raw sense data in table 800, the integrated voltage generated from the sense signal SS1 in the final time slot TS13 indicates the value of the sensor C121 because only the drive line DL12 is activated during this thirteenth time slot. Accordingly, from the raw sense data in table 800 the value Data13 indicates the value of the capacitive sensor C121. This value for the sensor C121 is then fed backward for use in determining the value of the adjacent (i.e., penultimate) capacitive sensor C111. This is seen in the penultimate row of table 804 where the determined value for the sensor C121 determined in time slot TS13 is subtracted from the raw sense data Data12 determined in time slot TS12 to thereby determine the value of the capacitive sensor C111. Next, in the preceding row in table 804 associated with the capacitive sensor C101, the value for the sensor C111 just determined is now fed backward and subtracted from the raw sense data Data11 determined in time slot TS11 to determine the value of the capacitive sensor C101. The method continues operation in this way until in row two of the table 804 the value for the capacitive sensor C21 is determined using the raw sense data Data2 from time slot TS2 (see table 800) by subtracting the value for the capacitive sensor C31 from this raw sense data. In the backward subtraction method of table 804, starting with the value for the capacitive sensor C121 determined in time slot TS13, the value of the prior capacitive sensor Cnm is determined using the raw sense data from the prior time slot TS. This is done until the method works backwards to the initial time slot TS1 during which only the drive line DL1 was activated so the sense signal SS1 generated during this initial time slot indicates the value of the capacitive sensor C11 without any subtraction being necessary, as was the case for the final time slot TS13.

Once again, after processing the raw sense data in table 800 according to the backward subtraction method illustrated in table 804, the values for all the capacitive sensors C11-C121 have been generated and the touch controller may determine whether any of these values indicate a touch is occurring at that sensor. The finger 502 in FIG. 5 is touching the touch panel 500 at the sensors C11, C21 and therefore the integrated voltage values generated for these sensors according to the backward subtraction method of table 804 would indicate a touch is occurring at these sensors.

Referring back to FIGS. 7 and 8 it is seen that the raw sense data Data1-Data13 in the table 800 generated according to the method of FIG. 7 is generated using time slots TS that include only 64 pulses. Thus, the drive signal DS applied to the drive line or drive lines DL includes only 64 pulses, which will result in the integrated voltages generated from the sense signals having smaller value (i.e., smaller amplitudes). These integrated voltage values are also more susceptible to noise, as discussed above, but may be suitable in many applications. With forward and backward subtraction methods just described, the scan time of the touch display 500 is further reduced. The scan time is for these methods given by 13 time slots times 64 pulses for the drive signal DS per time slot times 3 µS per pulse. Thus, the scan time equals (13×64×3 µS)=2496 µS=2.496 ms. When compared to the method of Figure Another embodiment of the present disclosure combines the methods just described with reference to tables 802 and 804 to improve the method of FIGS. 7 and 8. In this embodiment, the processed data of tables 802 and 804 is summed and then used to determine whether a touch is detected at each capacitive sensor C11-C112. In this way, although the raw sense data Data1-Data13 in table 800 is still based on 64 pulses per time slot TS, the value for each of the capacitive sensors C11-C121 is calculated in two different ways (i.e., through the forward-subtraction method and through the backward-subtraction method) and these two values summed to yield an integrated voltage value for each sensor has a signal strength or amplitude based on two times 64 pulses or 128 pulses. In this embodiment, the integrated voltage values for each sensor C11-C121 in the table 802 are summed with the values for each sensor in the table 804, and these summed values are then used to determine whether is occurring at each sensor. This embodiment, and the forward and backward subtraction embodiments, illustrated in FIGS. 7 and 8 are only depicted and explained for the sense line SL1, and these processes would be duplicated for each of the sense lines SL2-SL16 to generate integrated voltages for all sensors Cnm of the touch panel 500 and detect touches at all of these sensors so that the entire touch panel is scanned.

The touch panel 500 to which the methods of FIGS. 4-8 are applied includes twelve rows (drive lines DL1-DL12) and sixteen columns (sensor lines SL1-SL16) of sensors, but this is of course only by way of example. Methods according to embodiments of the present disclosure can be applied to touch panels of any size to reduce the overall scanning time of such panels.

Figure 9:
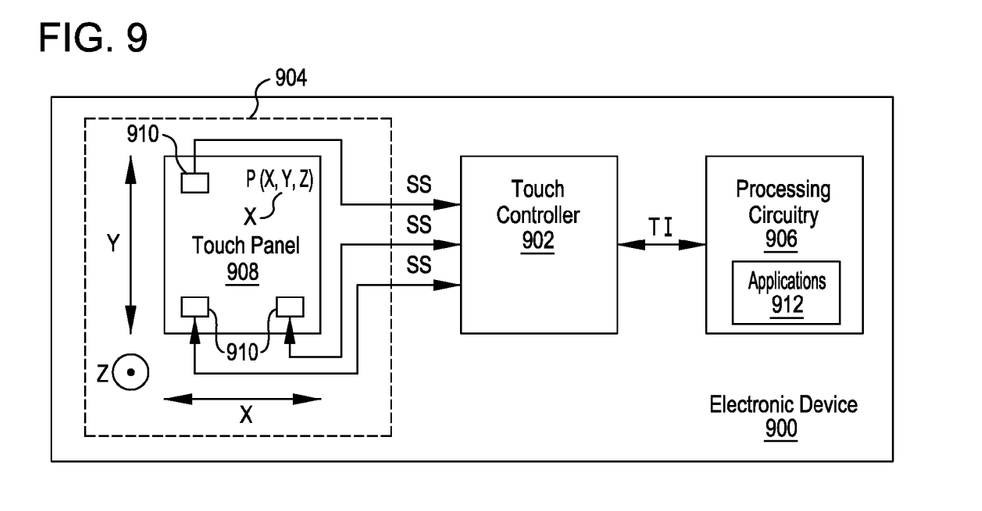
FIG. 9 is a functional block diagram of an electronic device including a touch controller that controls a touch panel to sense user touches using the methods of FIGS. 4-8 according to another embodiment of the present disclosure.

FIG. 9 is a functional block diagram of an electronic device 900 including a touch controller 902 that controls a touch screen 904 to sense user touches on the touch panel using the methods of FIGS. 4-8 according to another embodiment of the present disclosure. The electronic device 900 further includes processing circuitry 906 coupled to the touch controller 902 that controls the touch screen 904 to thereby detect touches or touch points P(X,Y,Z) applied on or above a touch panel 908 of the touch screen. In this way a user (not shown) of the electronic device 900 interfaces with and controls the operation of the electronic device. The electronic system or device 900 may be any type of electronic system, such as a personal computer, laptop computer, tablet computer, a smart phone, a portable music or video player, and so on. For the present description, the electronic device 900 is assumed to be a smart phone by way of example.

The touch screen 904 includes a touch display (not expressly shown in FIG. 9) such as a liquid crystal display (LCD) to which the touch panel 908 is attached or formed as an integral part of. The touch panel 908 corresponds to the touch panel 500, for example, and includes the drive and sense lines (not shown) for such a touch panel as previously discussed with reference to FIGS. 1-8. The capacitive sensors Cnm of the touch panel 908 that are formed by the drive and sense lines are represented in FIG. 9 as touch sensors 910, with only three touch sensors being shown merely by way of example and to simply the figure.

In operation of the touch screen 904, a user (not shown) generates a touch point P(X,Y,Z) through a suitable interface input, such as a touch event, hover event, or gesture event, using either his or her finger or an input device, such as an intelligent input device like an active stylus. The terms touch event, hover event, and gesture event will now be briefly described. A touch event is an interface input where the user's finger or input device is actually touching the surface of the touch panel 908, while hover and gesture events the user's finger or input device is within a sensing range above the surface of the touch panel but is not touching the surface of the panel. In a hover event the finger or input device may be stationary or moving while in a gesture event the finger or intelligent input device is moving in a singular or a plurality of predefined motions or constraints. The X-axis, Y-axis, and Z-axis are shown in FIG. 9 with the Z-direction being out of the page and orthogonal to the surface (i.e., the XY plane) of the touch panel 908. Thus, for a given touch point P(X,Y,Z), the X and Y values indicate the location of the touch point on the surface of the touch panel 908 while the Z value indicates the distance of the user's finger or input device from the surface, or simply whether the input device or finger is within the sensing range (Z=0 for touch events) from the surface.

In response to a touch point P(X,Y,Z), the sensors 910 generate sense signals that are sensed by the touch controller 902 which, in turn, processes these sense signals according to the methods of FIGS. 4-8 to generate touch information TI for the corresponding touch point. The touch information TI that the touch controller 902 generates for each touch point P(X,Y,Z) includes location information and event information identifying the type of interface input, namely whether the touch point P(X,Y,Z) corresponds to a touch event, hover event, gesture event, or some other type of event recognized by the touch controller. The location information includes an X-coordinate and a Y-coordinate that together define the XY location of the touch point P(X,Y,Z) on the surface of the touch panel 908.

Where the touch sensors 910 are capacitive sensors, as illustrated and described with reference to the embodiment of the touch panel in FIG. 5, the sensors are typically formed as an array of sensors from transparent patterned orthogonal conductive lines (not shown) formed on the surface, or integrated as part of, the touch display, as previously mentioned above. The intersections of the conductive lines form individual sensors Cnm and the touch controller 902 scans these sensors according to the methods of FIGS. 4 and 8. The touch controller 902 applied the drive signals DS according to any of the methods of FIGS. 4 and 8 and then senses the sense signals SS generated in response to the applied drive signals to generate the raw sense data, as shown and described with reference to FIGS. 4 and 8. The touch controller 902 then processes the raw sense data according to one or more of the methods of FIGS. 4 and 8 to identify the location and type of touch points P(X,Y,Z) on the touch panel 908. The touch controller 902 then provides touch information TI to the processing circuitry 906 indicating the detected touch or other input events on the touch panel 908.

The processing circuitry 906 is coupled to the touch controller 704 to receive the generated touch information TI, including the location of the touch points P(X,Y,Z) and the corresponding type of detected interface event (touch event, hover event, gesture event) associated with the touch point. The processing circuitry 906 executes applications or "apps" 912 that control the electronic device 900 to implement desired functions or perform desired tasks. These apps 912 executing on the processing circuitry 906 interface with a user of the electronic device 900 through the touch controller 902 and touch screen 904, allowing a user to start execution of or "open" the app and to thereafter interface with the app through the touch display and touch panel 908. The processing circuitry 906 represents generally the various types of circuitry contained in the electronic device 900 other than the touch screen 904 and touch controller 902. Where the electronic device 900 is a smart phone, for example, the processing circuitry 906 would typically include a processor, memory, Global Positioning System (GPS) circuitry, Wi-Fi circuitry, Bluetooth circuitry, and so on.

Even though various embodiments and advantages of the present disclosure have been set forth in the foregoing description, the present disclosure is illustrative only, and changes may be made in detail and yet remain within the broad principles of the present disclosure. Moreover, the functions performed by various components described above can be combined to be performed by fewer elements, separated and performed by more elements, or combined into different functional blocks depending upon the nature of the electronic system to which the present disclosure is being applied, as will be appreciated by those skilled in the art. At least some of the components described above may be implemented using either digital or analog circuitry, or a combination of both, and also, where appropriate, may be realized through software executing on suitable processing circuitry. It should also be noted that the functions performed by various components discussed above can be combined and performed by fewer elements or separated and performed by additional elements depending on the nature of the electronic device 900. Therefore, the scope of protection for the present disclosure is to be defined and limited only by the appended or subsequently submitted claims.

What is claimed is:

1. A method of controlling a touch panel including a plurality of drive lines, a plurality of orthogonal sense lines, and a plurality of sensors, the method comprising:
    simultaneously applying a drive signal to each of a group of drive lines of the touch panel, each of the drive signals being applied to a corresponding drive line in the group during a time slot and all the applied drive signals having the same electrical characteristics over the time slot;
    sensing over multiple time slots sense signals generated on the sense lines in response to the applied drive signals, the applied drive signals having the same electrical characteristics over all the multiple time slots;
    processing only the sense signals generated during the multiple time slots to detect touches of the touch panel;
    applying a drive signal to a first drive line during a first time slot; and
    applying a drive signal to a last drive line during a last time slot, wherein the first and last time slots are twice as long as the time slots between the first and last time slots.

2. The method of claim 1, wherein processing the sense signals to detect touches of the touch panel comprises:
    summing the sense signals for groups of time slots to generate summed sense signals; and
    detecting touches from the summed sense signals for each group of time slots.

3. The method of claim 2, wherein each group of drive lines is a pair of adjacent drive lines and each group of time slots is a pair of consecutive time slots.

4. A method of controlling a touch panel including a plurality of drive lines, a plurality of orthogonal sense lines, and a plurality of sensors, the method comprising:
    applying a drive signal on a first drive line for a first time slot;
    applying drive signals on groups of drive lines during a second time slot through an (N-1)th time slot, where N is the total number of drive lines;
    applying a drive signal on the Nth drive line for a final time slot, wherein the drive signals applied during each of the first time slot, second through (N-1)th time slot, and the final time slot have the same electrical characteristics during application of the drive signals in each of these time slots, wherein the first and final time slots each have a duration that is twice the duration of each of the second through (N-1)th time slots;
    sensing sense signals generated on the sense lines responsive to the drive signals; and
    processing the sense signals to sense touches on respective ones of the plurality of sensors of the touch panel.

5. The method of claim 4, wherein the electrical characteristics include the frequency and phase of the drive signals.

6. The method of claim 4, wherein processing the sense signals to detect touches on the touch panel comprises a forward-subtraction method.

7. The method of claim 4, wherein processing the sense signals to detect touches on the touch panel comprises a backward-subtraction method.

8. The method of claim 4, wherein processing the sense signals to detect touches on the touch panel comprises a forward-subtraction method and a backward-subtraction method.

9. A method of controlling a touch panel including a plurality of drive lines, a plurality of orthogonal sense lines, and a plurality of sensors, the method comprising:
    applying a drive signal on a first drive line for a first time slot;
    applying drive signals on groups of drive lines during a second time slot through an (N-1)th time slot, where N is the total number of drive lines;
    applying a drive signal on the Nth drive line for a final time slot;
    sensing sense signals generated on the sense lines responsive to the drive signals;
    processing the sense signals to sense touches on the touch panel; and
    wherein the first time slot and the final time slot are twice as long as the second through (N-1)th time slots.

10. The method of claim 9, wherein each group of drive lines comprises a pair of drive lines.

11. An electronic device, comprising:
    processing circuitry;
    a touch screen including a touch panel including a plurality of drive lines and a plurality of sense lines;
    a touch controller coupled to the processing circuitry and the touch screen, the touch controller is configured to,
        simultaneously apply a drive signal to each of a group of drive lines of the touch panel, each of the drive signals being applied to a corresponding drive line in the group during a time slot and all the applied drive signals having the same electrical characteristics over an entire duration of the time slot and the applied drive signals having the same electrical characteristics over all the time slots, wherein an initial time slot and a final time slot have durations that are twice as long as durations of the time slots between the initial and final time slots;
        sense signals generated on the sense lines in response to the applied drive signals over multiple time slots; and
        process only the sense signals generated in response to the applied drive signals having the same electrical characteristics to sense interface inputs applied to the touch panel.

12. The electronic device of claim 11, wherein the processing circuitry comprises smart phone processing circuitry.

13. The electronic device of claim 11, wherein the touch panel comprises a capacitive touch panel.

14. The electronic device of claim 11,
    wherein raw sense data is generated in response to the sensed signals on the sense lines; and
    wherein the touch controller is operable to perform a forward-subtraction of the raw data to sense interface inputs applied to the touch panel.

15. The electronic device of claim 11,
    wherein raw sense data is generated in response to the sensed signals on the sense lines; and
    wherein the touch controller is operable to perform a backward-subtraction of the raw data to sense interface inputs applied to the touch panel.

16. The electronic device of claim 11,
    wherein raw sense data is generated in response to the sensed signals on the sense lines; and
    wherein the touch controller is operable to perform both a forward-subtraction and a backward-subtraction of the raw data to sense interface inputs applied to the touch panel.

17. The electronic device of claim 16, wherein each group of drive lines comprises a pair of drive lines.

* * * * *